United States Patent [19]

Salamon et al.

[11] Patent Number: 5,521,702
[45] Date of Patent: May 28, 1996

[54] REUSABLE BIOCOMPATIBLE INTERFACE FOR IMMOBILIZATION OF MATERIALS ON A SOLID SUPPORT

[76] Inventors: Zdzislaw Salamon, 4480 W. Rockwood Dr., Tucson, Ariz. 85741; Richard A. Schmidt, 8518 E. 25th St., Tucson, Ariz. 85710; Gordon Tollin, 2050 W. Khaibar Pl., Tucson, Ariz. 85704; H. Angus Macleod, 2745 E. Via Rotonda, Tucson, Ariz. 85716-5227

[21] Appl. No.: 259,388

[22] Filed: Jun. 14, 1994

[51] Int. Cl.⁶ .................................................. G01N 21/01
[52] U.S. Cl. ........................ 356/244; 356/445; 422/82.05
[58] Field of Search ..................................... 356/244, 136,
356/445, 300, 318; 436/172, 165; 422/82.11,
82.05, 82.09; 435/287.1, 287.2, 287.9, 808;
428/66.6, 137–138

[56] References Cited

U.S. PATENT DOCUMENTS 2,780,131  2/1957  Lanneau et al. ...................... 356/136
5,164,589  11/1992  Sjödin ............................... 356/244 X
5,320,906  6/1994  Eley et al. .......................... 428/402.2
5,341,215  8/1994  Seher ................................. 356/445

OTHER PUBLICATIONS

Z. Salamon & G. Tollin; "Chlorphyll–Photosensitized Electron Transfer . . . ;" Aug. 10, 1993: Photochemistry and Photobiology, vol 58,#5 pp. 39–42.

Primary Examiner—Vincent P. McGraw
Assistant Examiner—K. P. Hantis
Attorney, Agent, or Firm—David G. Perry

[57] ABSTRACT

A method for the formation of a biocompatible film composed of a self-assembled bilayer membrane deposited on a planar surface. This bilayer membrane is capable of immobilizing materials to be analyzed in an environment very similar to their native state. Materials so immobilized may be subject to any of a number of analytical techniques.

9 Claims, 3 Drawing Sheets

REUSABLE BIOCOMPATIBLE INTERFACE FOR IMMOBILIZATION OF MATERIALS ON A SOLID SUPPORT

FEDERAL GOVERNMENT RIGHTS

This invention was made with Government support under contract number DOE-FG02-86ER13631 awarded by the Department of Energy. The Government has certain rights in this invention.

BACKGROUND OF THE INVENTION

1. Field of the Invention

This invention is related in general to the fields of immobilization of both inorganic and organic (including biological) materials on solid surfaces and the detection of their functional interactions. In particular, the invention provides a new method for immobilization of biological molecules on solid supports while providing a biocompatible environment, so that these materials may be detected in a native-like state using various well-known techniques and devices.

2. Description of the Related Art

For the detection of a material using any technique or device two goals should be met. First, the material should be immobilized in an effective manner such that accurate detection is possible. Second, the immobilized material should be able to be observed in a state that best approximates its native or in vivo condition. This is particularly important for biological materials where their in vivo conformation is crucial to both their quantitative and qualitative interactions with other molecules. Detection of any material utilizing available techniques and devices requires that the material be deposited on a solid surface. The conventional techniques for the immobilization of materials (including biological materials) on solid surfaces utilize any of the following methods:

(a) vacuum deposition;

(b) adsorption from solvents; and (c) physico-chemical and mechanical entrapment using different kinds of membrane systems.

The present invention utilizes a novel variant of the physico-chemical and mechanical entrapment method using a self-assembling membrane system. Specifically, it uses a self-assembled bilayer, which resembles a freely suspended lipid bilayer membrane, deposited on a solid support. This bilayer membrane provides the means for the immobilization of the material to be examined. Prior techniques utilizing bilayers for entrapment of the target material have been formed by the Langmuir-Blodgett technique. This technique produces a monomolecular Langmuir-Blodgett film. This film has a compressed surface layer of molecules that are amphiphilic (i.e. they have polar ends that readily interact with an aqueous solution and nonpolar ends that do not), thus their alignment is highly regularized and dense. The dense structure of the Langmuir-Blodgett film incorporates less fluid and behaves more like a rigid semi-solid structure. As a result, any material incorporated into this film is less mobile. For organic (i.e. biological materials) this means that they are less able to freely interact with one another and hence they behave less as they would in their native (in vivo) environment. If one is examining the interaction between various molecules this limitation can be a great detriment to any detection device utilizing a Langmuir-Blodgett film.

Unlike a Langmuir-Blodgett film, a self-assembled, freely suspended lipid bilayer behaves more like the lipid bilayer membranes found in vivo in cells. Another important feature of the freely suspended bilayer membranes is that solvent molecules are involved in their formation and therefore can be experimentally manipulated. This type of manipulation is not possible with Langmuir-Blodgett films. In spite of their advantages, freely suspended lipid bilayers have several disadvantages, their extreme fragility and size. This fragility and tendency to form small structures (usually less than 1 mm in diameter) makes it difficult to utilize the bilayers in any of the current analytical systems. If membranes composed of freely suspended lipid bilayers could be formed uniformly on a planar surface, they would be able to be utilized in a variety of currently available analytical techniques. The present application is directed to a method of forming these self-assembled freely suspended lipid bilayers deposited on planar solid surfaces such that they cover a relatively large area yet retain the desirable characteristics mentioned above.

BRIEF SUMMARY OF THE INVENTION

One objective of this invention is to provide a biocompatible film composed of a self-assembled freely suspended bilayer membrane deposited on a large planar surface composed of a hydrophilic material.

Another objective of this invention is to provide a biocompatible membrane capable of immobilizing biological materials on a solid surface by means other than mechanical entrapment or chemical interactions while at the same time preserving the in vivo structure and therefore the in vivo activity of the materials so immobilized.

A further goal of the invention is a biocompatible membrane that is capable of being reused.

Still another objective of the invention is to provide a biocompatible membrane capable of being deposited on a planar surface such that it can be analyzed via a variety of transduction devices (i.e. optical, electrochemical, etc.).

A final objective of this invention is the realization of the above mentioned goals in an economical and commercially viable manner. This is done by utilizing materials and methods of manufacture that are either already available in the open market or can be developed at competitive prices.

According to these and other objectives, the present invention consists of a self-assembled freely suspended bilayer membrane formed across an aperture of a membrane holder and deposited on the surface of a thin semiconducting or metal film or films. Once the bilayer is formed and deposited, the material to be immobilized can be introduced and analyzed using various techniques.

Various other purposes and advantages of the invention will become clear from its description in the specification that follows and from the novel features particularly pointed out in the appended claims. Therefore, to accomplishment of the objectives described above, this invention consists of the features hereinafter illustrated in the drawings, fully described in the detailed description of the preferred embodiment and particularly pointed out in the claims. However, such drawings and descriptions disclose but one of the various ways in which the invention may be practiced.

DESCRIPTION OF THE PREFERRED EMBODIMENT OF THE INVENTION

This invention is directed at developing a reusable biocompatible interface that will allow certain materials (in particular biological materials) to be immobilized and deposited on a solid support. These materials then can be examined analytically using any one of several currently available techniques. One of the principal advantages of the interface that is the subject of this application is that due to its structure, the target material is allowed to behave and interact in a way very much like it would in vivo.

Figure 1:
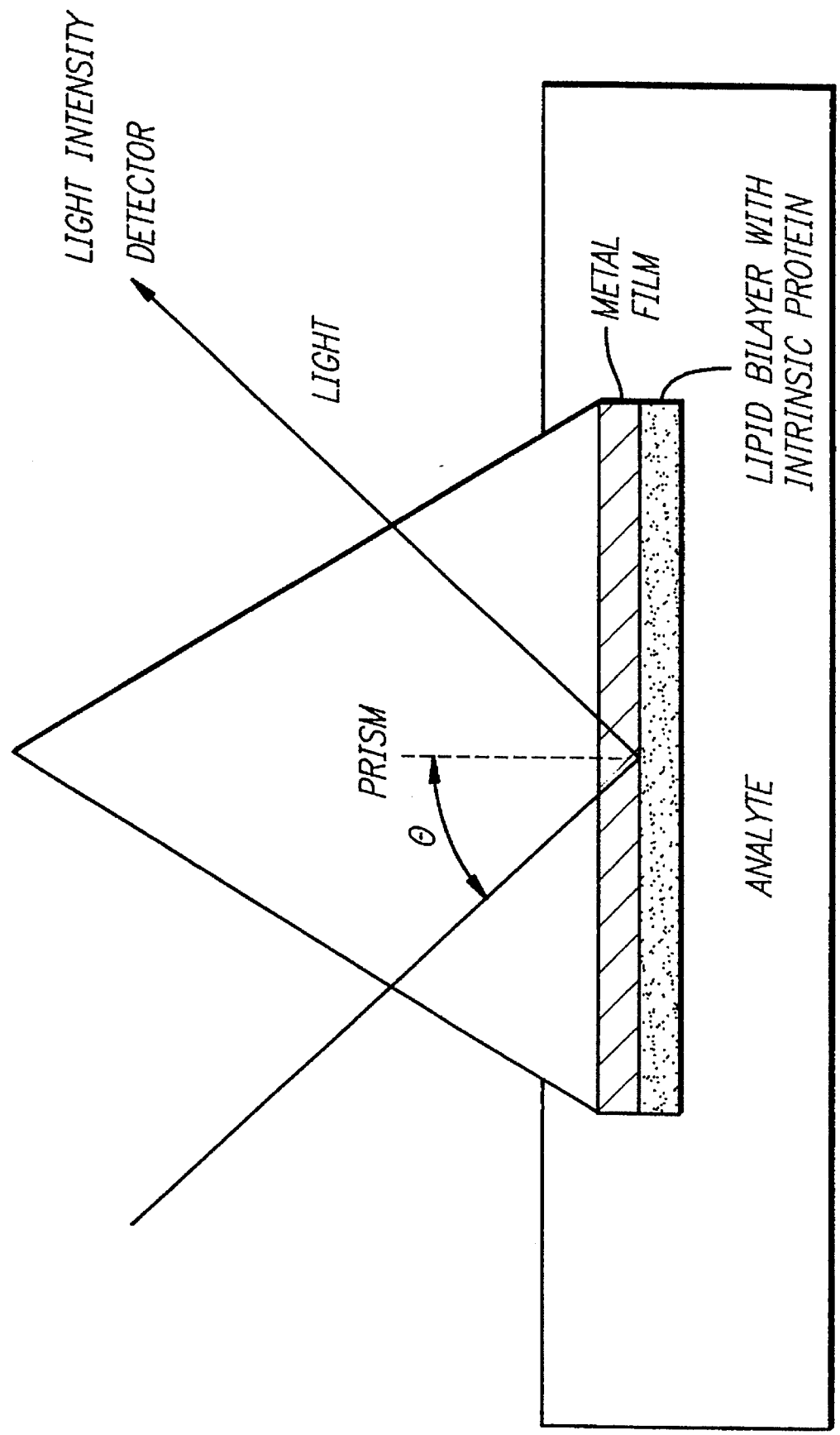
FIG. 1 is a side view schematic representation showing the relationship of the incident light beam to the metal film support and the lipid bilayer.

Referring to the drawings, wherein like parts are identified with like symbols throughout this specification, FIG. 1 illustrates in schematic form the orientation of the reusable biocompatible interface to the solid support onto which it will be deposited. It also shows the orientation of the interface to the incident light ray and detector array that is utilized in the analysis in the analysis in the preferred embodiment.

Figure 2:
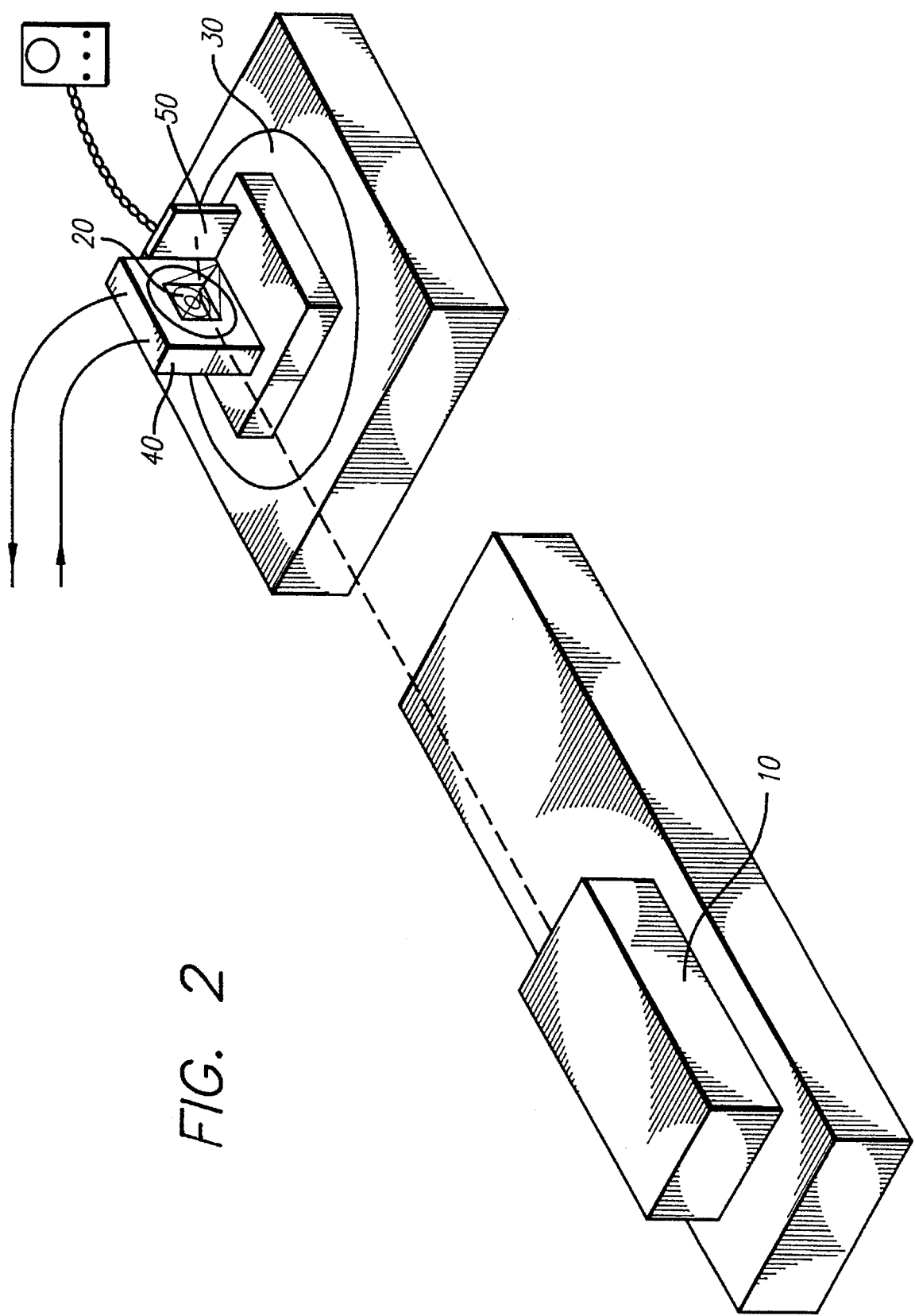
FIG. 2 is a schematic partial view of the preferred embodiment of the invention, illustrating the surface plasmon resonance biosensor system composed of a laser light source and mounted on a rotating table a prism, a plasmon cell and a photodetector device.

FIG. 2 illustrates a schematic partial view of the surface plasmon resonance biosensor system. It is composed of a light source 10 made up of a low power laser with an optical arrangement shaping and then directing the laser beam. The beam is directed toward the prism 20 which is attached to a rotating table 30. The light is then totally reflected from the bottom surface of the prism 20 which is coated with a metal film and a lipid bilayer containing the immobilized target material playing the role of the sensing areas of a sensor unit 40 which is in contact with an aqueous solution and is imaged on a two-dimensional photodetector device 50. The electric signals created by the photodetector device 50 are processed and stored in a computer. The computer controls rotation of the rotating table 30.

Figure 3:
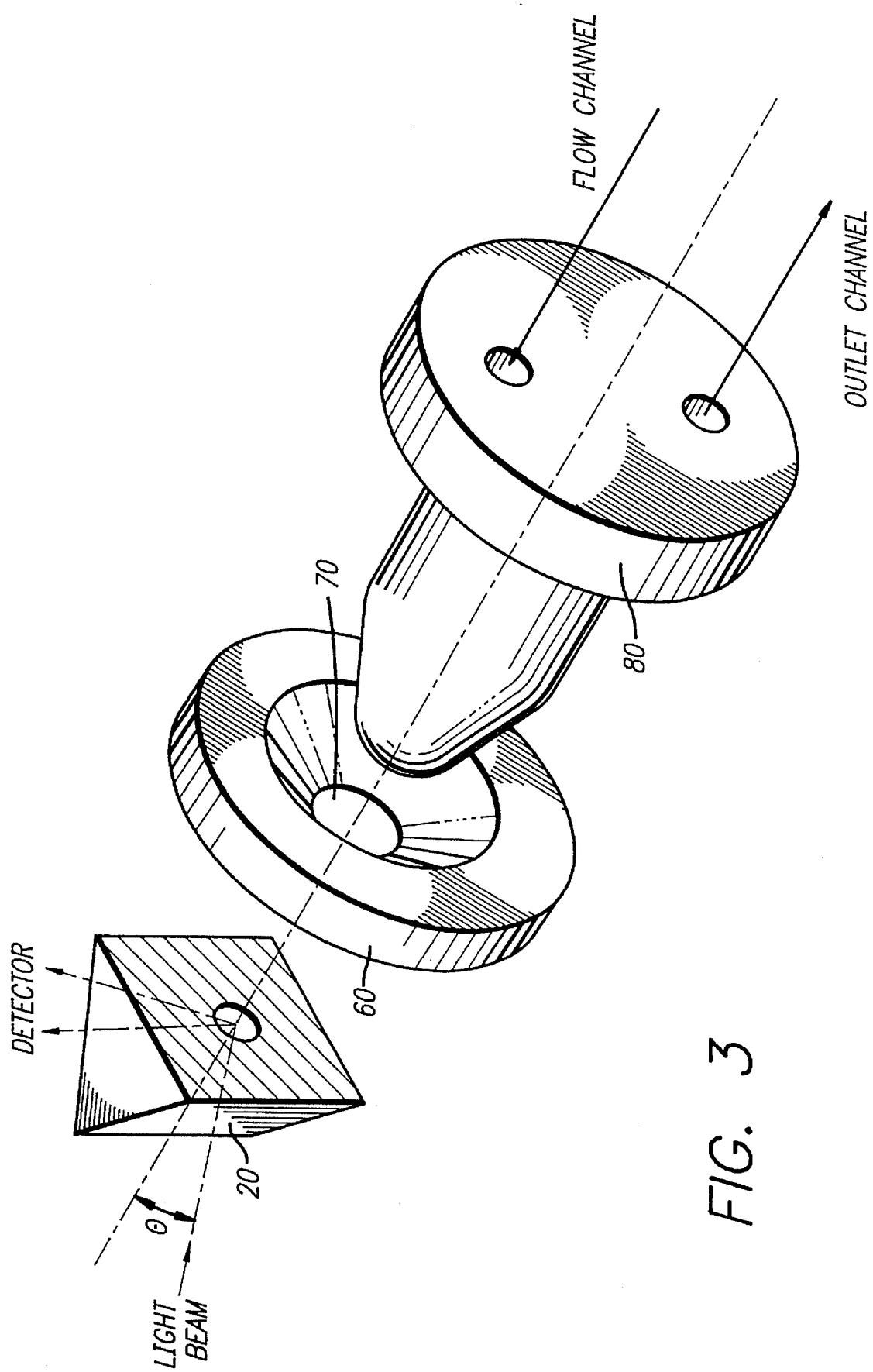
FIG. 3 is a schematic exploded view of the preferred embodiment of the invention illustrating in more detail the design of the cell compartment coupled to the sensor unit.

FIG. 3 shows a schematic exploded view of the cell compartment coupled to the sensor unit 40. The cell compartment comprises a lipid bilayer holder 60 made of a hydrophobic material with a shaped aperture 70 on it and a back cover plate 80 of the cell with the flow and outlet channels in it. The front cover of the cell is provided by the prism 20 coated with a metal film or films.

In the preferred embodiment illustrated in the drawings, the biocompatible interface is utilized in a surface plasmon resonance spectrometer. This device is based upon the attenuated total reflection technique. It consists of a low power laser light source 10 with routine optical parts for shaping the laser beam, a cell compartment composed of a sensor unit 40 and a prism 20, and a photodetector device 50. The cell compartment and the light detector are mounted on a rotating table 30. The rotation of this table 30 is controlled by a computer which receives its input from the photodetector device 50. It is the rotation of this table 30 that varies the incident angle of the light from the low power laser light source 10.

The surface plasmon resonance (SPR) phenomenon which provides the index of measurement for this apparatus, is very sensitive to the optical conditions which exist within a few hundred angstroms of the metal surface. Resonance causes the energy of the incident photons to be absorbed, and less light is thereby reflected by the interface at the metal surface. Thus, the measurement of reflectance of the light beam as a function of incident angle produces the SPR curve, with very sharp minimum at the resonance angle. This feature of the phenomenon can be used to detect small quantities of mass present at the metal bilayer membrane interface. This device can therefore monitor processes of adsorption and desorption at the metal bilayer interface, with particular application to biological materials involving lipid bilayer membrane-protein and protein-protein interactions.

In the preferred embodiment, the bilayer lipid membrane is self-forming. The method of bilayer membrane formation involves spreading a small amount of a biocompatible material solution, called the bilayer membrane forming solution (preferably a lipid solution), across an orifice (larger than 2 mm in diameter) in the membrane holder which separates a solid support from the aqueous phase. The biocompatible material may be any material that possesses the ability to self-assemble and form a bilayer membrane. The surface of the solid support, being highly hydrophilic, attracts the polar groups of the bilayer forming molecules, thus forming an adsorbed well-organized monolayer with the hydrophobic parts oriented toward the bilayer forming solution phase. Subsequent to this first step of the bilayer formation, the main body of the sample cell is filled with the appropriate aqueous solution which causes the excess bilayer forming solution to be taken up on the aqueous-air interface. This initiates the second step, which involves a thinning process as a consequence of the various driving forces, similar to the case of the freely suspended planar lipid bilayer membranes. When the film approaches molecular dimensions in thickness, London-van der Waals forces accelerate the thinning process until these forces are opposed at equilibrium by the steric repulsion forces. Also involved is the hydrophobic component of the solvent of the biocompatible material, which dilutes the final concentration of the bilayer forming material in the bilayer membrane. This bilayer membrane is composed of a hydrophobic interior surrounded by two hydrophilic exteriors.

Once the planar membrane is formed on the solid support surface, the material to be immobilized and analyzed can be introduced into the system. Water soluble (organic and inorganic) molecules can be immobilized on the surface of the bilayer membrane either by chemical binding or electrostatic or hydrophobic interactions. The immobilization of one or more types of molecules within a bilayer structure is provided according to the following methods: (a) for small inorganic and organic molecules freely soluble in hydrophobic solvents by prior solution of such molecules in the bilayer forming solution. (b) for larger molecules, in particular for the intrinsic membrane proteins, by transferring the molecules from micelles to the bilayer membrane using the dilution technique.

Once immobilized either in or on the bilayer membrane, the molecules to be examined are free to interact with other molecules. Since these molecules are not unduly constrained by this immobilization, they are relatively free to interact with other molecules in a manner very similar to how they would interact in vivo.

Thus, this invention provides a means for the immobilization of material such that it can be subjected to any of a number of analytical techniques. These materials so immobilized are free to exist in a state that closely approximates their native one. As a result, interactions between molecules immobilized via this system will more closely resemble the nature of these interaction in vivo.

Various other changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is therefore not to be limited to the details disclosed herein, but is to be accorded the full scope of the claims so as to embrace any and all equivalent apparatus and methods.

What we claim is:

1. A reusable biocompatible interface for immobilization of materials on a solid support, comprising:
   (a) first, a self-assembled bilayer membrane wherein the exterior is hydrophobic and the interior is hydrophobic in nature;
   (b) second, a holder with a shaped aperture, where said aperture is shaped to allow the formation and maintenance of the self-assembled bilayer membrane;
   (c) third, a solid support on which rests the holder with the shaped aperture and the self-assembled bilayer membrane contained within the shaped aperture.

2. The holder with a shaped aperture described in claim 1, wherein said holder is made of a hydrophobic material.

3. The holder with a shaped aperture described in claim 2, wherein said holder is composed of a hydrocarbon polymer.

4. The solid support described in claim 1, wherein said support is made of glass, plastic or quartz.

5. The solid support described in claim 4, wherein said support has a thin film deposited on it.

6. The solid support described in claim 5, wherein the thin film or films are composed of metal or a semi-conducting material with a hydrophilic surface.

7. The reusable biocompatible interface described in claim 1 further comprising:
   (a) first, an energy source;
   (b) second, a means to shape and direct the emitted energy;
   (c) third, a prism;
   (d) fourth, a detector for sensing the intensity of the reflected energy passing from the energy source, in one side of the prism, through the sample area, out the opposite side of the prism and onto the detector;
   (e) fifth, a rotating table upon which the prism, the sample and the detector rest.

8. The reusable biocompatible interface described in claim 7, wherein the energy source is a low power laser and the detector senses light intensity.

9. The reusable biocompatible interface described in claim 7, wherein the detector array senses electrochemical changes.

* * * * *